US009872714B2

(12) United States Patent
Govaers

(10) Patent No.: US 9,872,714 B2
(45) Date of Patent: Jan. 23, 2018

(54) METHOD AND DEVICE FOR ENDOSCOPICALLY ASSISTED ARTHROPLASTY

(75) Inventor: Kristoffel Govaers, Kalmthout (BE)

(73) Assignee: Kristoffel Govaers, Kalmthout (BE)

(*) Notice: Subject to any disclaimer, the term of this patent is extended or adjusted under 35 U.S.C. 154(b) by 908 days.

(21) Appl. No.: 13/576,495

(22) PCT Filed: Feb. 1, 2011

(86) PCT No.: PCT/EP2011/051347
§ 371 (c)(1),
(2), (4) Date: Aug. 1, 2012

(87) PCT Pub. No.: WO2011/092337
PCT Pub. Date: Aug. 4, 2011

(65) Prior Publication Data
US 2012/0310248 A1  Dec. 6, 2012

(30) Foreign Application Priority Data
Feb. 1, 2010  (GB) .................................. 1001573.3

(51) Int. Cl.
*A61B 17/15* (2006.01)
*A61B 17/16* (2006.01)
(Continued)

(52) U.S. Cl.
CPC .............. *A61B 17/88* (2013.01); *A61B 17/15* (2013.01); *A61B 17/164* (2013.01);
(Continued)

(58) Field of Classification Search
CPC .... A61B 17/15; A61B 17/164; A61B 17/1668
See application file for complete search history.

(56) References Cited

U.S. PATENT DOCUMENTS 4,686,972 A  8/1987 Kurland
5,005,559 A  4/1991 Blanco et al.
(Continued)

FOREIGN PATENT DOCUMENTS

DE  19719052 C1  8/1998
EP  1588669 A1  10/2005
(Continued)

OTHER PUBLICATIONS

Patent Examination Report No. 1 in Australian Patent Application 2011209483, dated Aug. 30, 2013.
(Continued)

*Primary Examiner* — Nicholas Woodall
(74) *Attorney, Agent, or Firm* — Bacon & Thomas, PLLC

(57) ABSTRACT

The invention provides a mounting system for instruments for use in medulloscopy. The mounting system includes a positioning system adapted for being mechanically attached to a bone, and at least one instrument holder attached to the positioning system, the instrument holder being adapted for holding one or more instruments for being used during bone surgery in a medullary canal. Due to the positioning system which may be mechanically attached to the bone, and due to the instrument holder for holding instruments which is attached to the positioning system, a surgeon has both hands available for operating on the patient.

13 Claims, 14 Drawing Sheets

(51) Int. Cl.
*A61B 17/17* (2006.01)
*A61B 17/88* (2006.01)
*A61B 17/90* (2006.01)
*A61B 90/00* (2016.01)

(52) U.S. Cl.
CPC ...... *A61B 17/1668* (2013.01); *A61B 17/1717* (2013.01); *A61B 17/8847* (2013.01); *A61B 2017/90* (2013.01); *A61B 2090/373* (2016.02)

(56) References Cited

U.S. PATENT DOCUMENTS

| | | | |
|---|---|---|---|
| 5,645,519 A * | 7/1997 | Lee et al. | 600/114 |
| 5,649,930 A | 7/1997 | Kertzner | |
| 5,908,423 A | 6/1999 | Kashuba et al. | |
| 6,018,094 A * | 1/2000 | Fox | A61B 10/00 606/191 |
| 6,402,511 B1 * | 6/2002 | Calderwood | 433/29 |
| 2003/0171756 A1 * | 9/2003 | Fallin | A61B 17/175 606/80 |
| 2005/0149028 A1 | 7/2005 | Birkbeck et al. | |
| 2005/0245934 A1 | 11/2005 | Tuke et al. | |
| 2008/0161820 A1 | 7/2008 | Wack et al. | |
| 2008/0183179 A1 | 7/2008 | Siebel et al. | |
| 2008/0288006 A1 | 11/2008 | Brannon | |
| 2009/0149707 A1 * | 6/2009 | Brannon | 600/114 |
| 2009/0254130 A1 | 10/2009 | Wotton, III | |

FOREIGN PATENT DOCUMENTS

| | | |
|---|---|---|
| EP | 1813215 A1 | 8/2007 |
| GB | 2442441 A | 4/2008 |
| JP | H07-328026 A | 12/1995 |
| JP | H08-506260 A | 7/1996 |
| JP | H10-192297 A | 7/1998 |
| JP | H10-328205 A | 12/1998 |
| JP | 2009-536086 A | 10/2009 |
| WO | 2007137327 A1 | 12/2007 |
| WO | 2009098086 A1 | 8/2009 |

OTHER PUBLICATIONS

International Search Report for PCT/EP2011/051347, dated May 19, 2011.
Japanese Office Action dated Aug. 4, 2015 for JP 2012-551589, and English translation thereof.
Canadian Office Action dated Jun. 13, 2016, for CA 2,788,646.

* cited by examiner

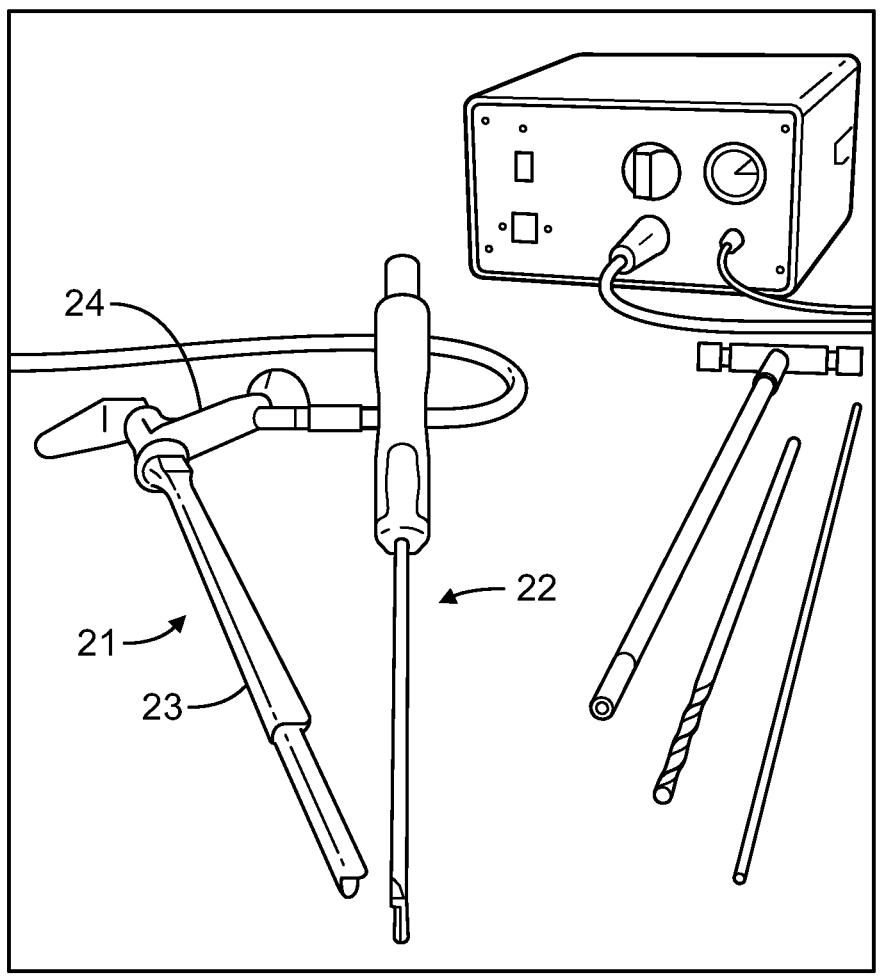
FIG. 2 - PRIOR ART

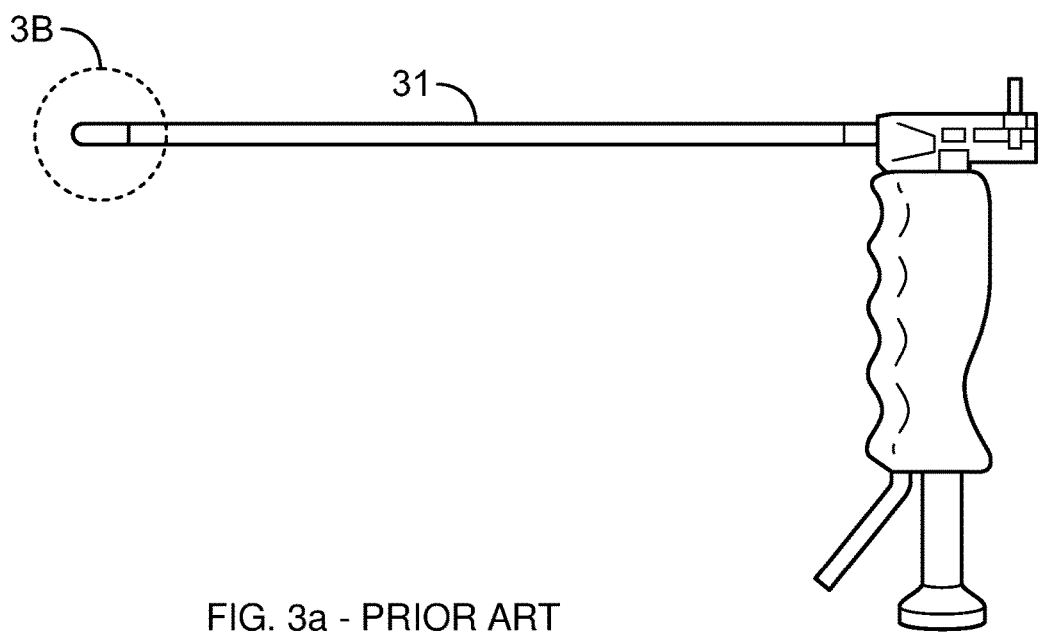
FIG. 3a - PRIOR ART
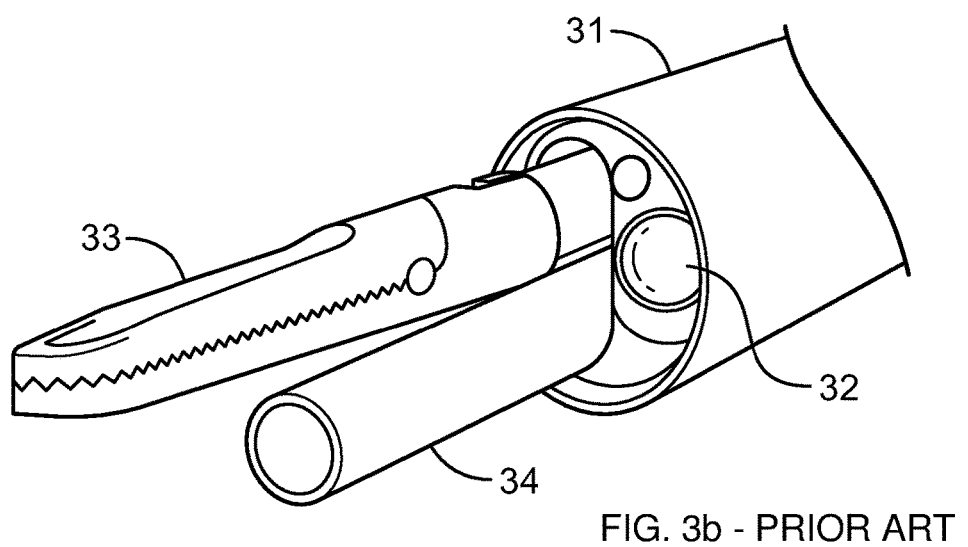
FIG. 3b - PRIOR ART

METHOD AND DEVICE FOR ENDOSCOPICALLY ASSISTED ARTHROPLASTY

FIELD OF THE INVENTION

The present invention relates to an endoscopic resecting system which removes osseous tissue and/or grouting agent from a bone canal. In particular embodiments, the present invention relates to an endoscopic resecting system which removes osseous tissue and/or grouting agent such as methyl-methacrylate (bone cement) from the human body femoral canal during primary hip surgery or revision hip surgery, for example to treat arthritis of the hip joint.

BACKGROUND OF THE INVENTION

Arthroplasty is an operation to restore as far as possible the integrity and functional power of a joint. An artificial joint is created for example to correct advanced degenerative arthritis.

A conventional method for treatment of severe arthritis of the hip involves performing an internal amputation of the proximal end 11 of the femur 10 (see FIG. 1), and its replacement with an appropriately shaped metallic device. A spacer or grouting agent, such as for example methyl-methacrylate (bone cement) is used to seat and secure the metal implant into the femur. This is called primary total hip arthroplasty.

After several years, the metal implant needs to be replaced by a new one. The grouting agent (bone cement) needs to be removed from the femoral canal. This is a particularly problematic, lengthy and tedious procedure. It can be associated with severe complications like perforation of the femoral canal or femoral fractures (with a rate of up to 18%). Numerous devices have been advocated to facilitate cement removal.

Traditionally actions within the marrow canal of the bone in primary and revision hip arthroplasty have been performed blindly. Problems encountered were that sizing of the femoral stem was not always accurate, and that the canal was not always dry before placing the metallic implant. In revision hip arthroplasty it was very difficult to remove the grouting agent (cement), especially distally in the femoral canal.

Intramedullary bone endoscopy, intraosseus endoscopy, bone marrow endoscopy and medulloscopy are synonyms to describe a more recently used visual inspection method and system of the medullary canal. Medulloscopy, a term first introduced by Roberts, means endoscopic visual inspection of the intramedullary canal of a long bone. Most of the clinical experience so far focuses on endoscopically assisted cement removal in revision hip arthroplasty. Endoscopy has also been used to assist pedicle screw placement, core decompression, autogenous bone grafting, canal preparation in primary hip arthroplasty and inspection of the medullary canal in septic nonunions of long bones.

Several devices have been proposed. One solution is provided by M. Porsch (OrthoScope, available from Swiss OrthoClast) in 1999 (OrthoScope, available from Swiss OrthoClast) and provides a rigid camera system 21 and a separate chiseling system 22. It is a disadvantage of the endoscopic resection system of FIG. 2 that the camera system, in view of its long straight arm 23 and heavy camera part 24, requires manipulation with two hands, which implies that it has to be manipulated by an assistant. Furthermore, a scope based on Hopkins-lenses always has to be of a well-defined length and is always straight because of the optical physics of this type of lenses, although the femoral shaft is somewhat bowed. The shape of the femoral canal as well as its diameter differ from patient to patient. Such stiff scope cannot be deformed and is very vulnerable, especially when being in close proximity with the chiseling system 22. As such, a good view with the scope, deep down the shaft, cannot be obtained.

Another solution is provided by M. Oberst in 2002 (Intramedullary bone endoscopy—IBE) and is illustrated in FIG. 3a and FIG. 3b. A hollow rigid tube 31 is introduced into a bone canal. The rigid tube 31 is at its front extremity provided with a camera system 32 (Hopkins lens). Instruments, such as for example a grasping forceps 33 and a suction tube 34, are introduced into the rigid tube 31. A disadvantage of this solution is that it has limited ergonomy.

SUMMARY OF THE INVENTION

It is an object of embodiments of the present invention to provide a good endoscopic resection system for bone surgery.

The above objective is accomplished by a device and method according to the present invention.

In a first aspect, the present invention provides a mounting system for instruments for use in medulloscopy. The mounting system comprises a positioning system adapted for being mechanically attached to a bone, and at least one instrument holder attached to the positioning system, the instrument holder being adapted for holding one or more instruments for being used during bone surgery in a medullary canal.

Due to the positioning system which may be mechanically attached to the bone, and due to the instrument holder for holding instruments which is attached to the positioning system, a surgeon has both hands available for operating on the patient. This is different from prior art devices where the surgeon needs to allocate one hand to hold and direct a scope. This is also different from other prior art devices where an assistant needs to hold the scope or where a scope is fixed on a static support not forming part of the patient, such as for example a bed or a frame attached to a bed.

In a mounting system according to embodiments of the first aspect of the present invention, the positioning system may be a spring system adapted for being fixed in the medullary canal.

In alternative embodiments, the positioning system may be a clamp adapted for being attached onto the bone. The clamp may be adapted for being placed on a trochanter.

In yet alternative embodiments, the positioning system may be a pinning system adapted for being pinned in the bone.

Mounting systems according to embodiments of the present invention are easily applicable, easily removable, and cause no damage to the bone.

In a second aspect, the present invention provides an endoscopic resection system comprising a mounting system according to any of the embodiments of the first aspect of the present invention, and an endoscope for visualizing a medullary canal.

Such endoscopic resection system is advantageous in that it allows to carry out a minimally invasive medical procedure.

In an endoscopic resection system according to embodiments of the present invention, the scope is a flexible scope. Such flexible scope allows the use inside a bone channel which is not completely straight. In particular embodiments, the flexible scope may be provided with a sleeve for protecting the scope during surgical use. The protection may be against scratching or other damaging of the scope. In these and other embodiments, the sleeve may be so as to have a memory function for flexure. The sleeve may for example be made from a memory shape material.

An endoscopic resection system according to embodiments of the present invention may furthermore comprise a suction tube. Such suction tube may be used for example for removal of fluids like for instance blood, marrow, water.

An endoscopic resection system according to embodiments of the present invention may furthermore comprise a powered or non-powered device such as for example a grasping device, a drill, a chiseling device.

In a third aspect, the present invention provides the use of a mounting system according to any of the embodiments of the first aspect of the present invention or of an endoscopic resection system according to any of the embodiments in any of orthopedic surgery, knee surgery, upper arm surgery, hip surgery, e.g. hip arthroplasty, pelvic surgery, or other bone surgery in human or animal patients.

In a fourth aspect, the present invention provides the use of a flexible endoscope during hip surgery. Such use may include the use of a mounting system according to any of the embodiments of the first aspect of the present invention.

In a fifth aspect, the present invention provides a method for preparation of a minimally invasive method for performing bone surgery, the preparation method comprising mechanically attaching a positioning system to a bone, an instrument holder being attached to the positioning system, attaching one or more instruments for being used during bone surgery to the instrument holder.

Particular and preferred aspects of the present invention are set out in the accompanying independent and dependent claims. Features from the dependent claims may be combined with features of the independent claims and with features of other dependent claims as appropriate and not merely as explicitly set out in the claims.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

BRIEF DESCRIPTION OF THE DRAWINGS

FIG. 2 illustrates one prior art endoscopic resection system comprising a rigid camera system and a separate chiseling system, known as the Swiss OrthoClast system.

FIG. 3a illustrates another prior art endoscopic resection system, the Intramedullary Bone Endoscope (IBE), comprising a rigid tube through which the operation instruments are guided. FIG. 3b is an enlarged view of part of the endoscopic resection system of FIG. 3a.

Figure 1:
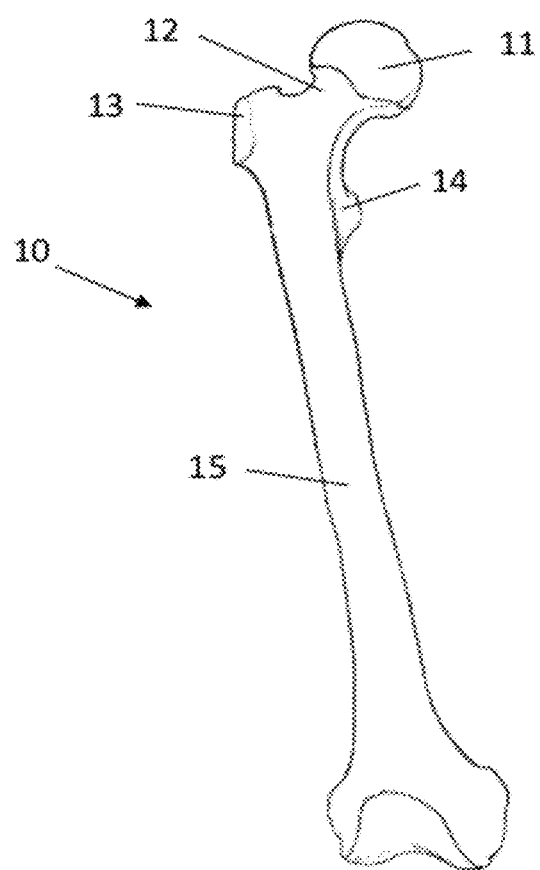
FIG. 1 illustrates a thigh bone of a human body, a femur.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The detailed description of the present invention relates to endoscopically assisted hip surgery, more particularly for example hip arthroplasty. However, the present invention is not limited thereto and also includes endoscopically assisted bone surgery in other bones having a medullary canal, both in human beings and in animals, such as for example a human upper arm or humerus. Embodiments of the present invention may be used in other types of bone surgery, such as for example treatment of bone infection (osteomyelitis), reduction and fixation of fractures, treatment of bone infarction (osteonecrosis), treatment of tumors and systemic diseases, reconstructive surgery following amputations, including non-anatomical reconstructions such as reconstructions using technical devices instead of human or animal bones.

The proximal femur or femoral bone 10 (FIG. 1) is the substrate to work on when performing endoscopically assisted hip surgery in accordance with embodiments of the present invention. The upper end of the femoral bone 10, as illustrated in FIG. 1, comprises the femoral head 11, the femoral neck 12, the greater trochanter 13 and the lesser trochanter 14 which are located at the junction of the neck 12 with the body 15.

During first time hip surgery (primary total hip arthroplasty), the femoral head 11 is removed from the femur 10, and the medullary canal inside the femur (not illustrated in FIG. 1) is opened by means of suitable instruments, e.g. chiseling instruments. Thereafter, the femoral head is replaced by an appropriately shaped replacement device, for example a metallic device. A spacer or grouting agent, such as for example methyl-methacrylate (bone cement) is used to seat and secure the replacement device, e.g. metal implant, into the medullary canal. During revision hip surgery, similar steps are carried out, whereby opening the medullary canal comprises removing previously applied grouting agent.

In accordance with embodiments of the present invention, the preparation of the medullary canal is performed in an endoscopically assisted way. This is done in order to eliminate blind steps in the surgical procedure, thus reducing the number of complications during hip revision surgery, such as for example fracture or perforation of the thigh bone.

In accordance with embodiments of the present invention, a mounting system is provided for mounting instruments for use in bone surgery. The mounting system comprises on the one hand a positioning system adapted for being mechanically attached to a bone, for example to the femur, and on the other hand an instrument holder attached to the positioning system, the instrument holder being adapted for holding one or more instruments for being used during bone surgery in a medullary canal.

Figure 4:
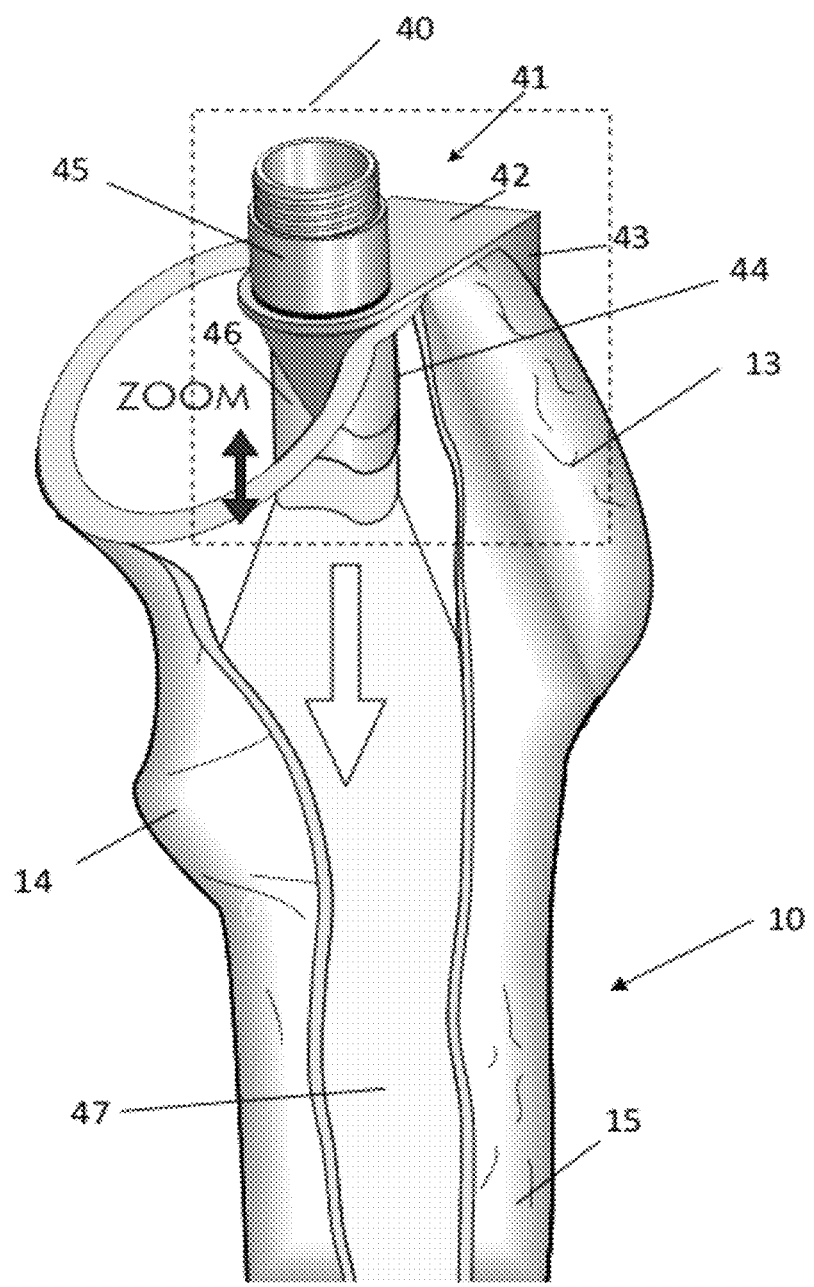
FIG. 4 illustrates a first embodiment of a mounting system according to the present invention.

A first embodiment of a mounting system 40 according to embodiments of the present invention is illustrated in FIG. 4. FIG. 4 illustrates part of a partially broken away femur 10 of which the femoral head is removed. By illustrating the femur partially broken away, the medullary canal 47 becomes visible.

The mounting system 40 comprises a positioning system 41 for being mechanically attached to the bone 10. In the embodiment illustrated, the positioning system 41 is a clip which has a shape adapted for clipping over the upper part of the opened bone, e.g. in particular embodiments a shape adapted for clipping over the greater trochanter 13. Therefore, the clip 41 has a back 42 and two legs 43, 44. The back 42 rests on or slightly above the upper part of the opened bone, e.g. on or slightly above the greater trochanter 13, and the two legs 43, 44 clip over the upper part of the opened bone, e.g. over the greater trochanter 13, at either side thereof. This means that one leg 43 is provided at the outside of the bone 10, and the other leg 44 is provided at the inside of the bone 10. The leg 44 at the inside of the bone 10, i.e. in the medullary canal 47, is preferably shaped and mounted such that it resides as closely as possible against an inner wall of the medullary canal 47, so as to leave as much space as reasonably possible for introducing instruments into the medullary canal 47. In particular embodiments of the present invention (not illustrated in FIG. 4), the leg 44 may be flat so as to occupy as little room as possible.

The mounting system 40 furthermore comprises an instrument holder 45 attached to the positioning system 41. In embodiments of the present invention, the instrument holder 45 may be attached to the back 42 of the positioning system 41. In alternative embodiments, the instrument holder 45 may be attached to one of the legs 43, 44 of the positioning system 41. In the embodiment illustrated in FIG. 4, the instrument holder 45 is a tube, for example a cylindrical tube, adapted for containing a scope 46. This scope 46 may be a fixed scope. The scope 46 may have a zoom function. In the embodiment illustrated in FIG. 4, the scope 46 is present only at the top of the medullary canal 47, but if its properties are good enough, it can provide to the surgeon images of sufficient quality. In the embodiment illustrated in FIG. 4, the scope 46 forms the second leg 44, however, this is not required. A separate leg 44, separate from the scope 46, may be provided. In alternative embodiments, as illustrated in FIG. 19, a scope, for example a flexible scope, can be introduced through the instrument holder 45, from the outside of the bone 10 into the medullary canal 47, as deep into the medullary canal as required for the surgeon to work, e.g. over substantially the complete depth of the canal 47.

Figure 19:
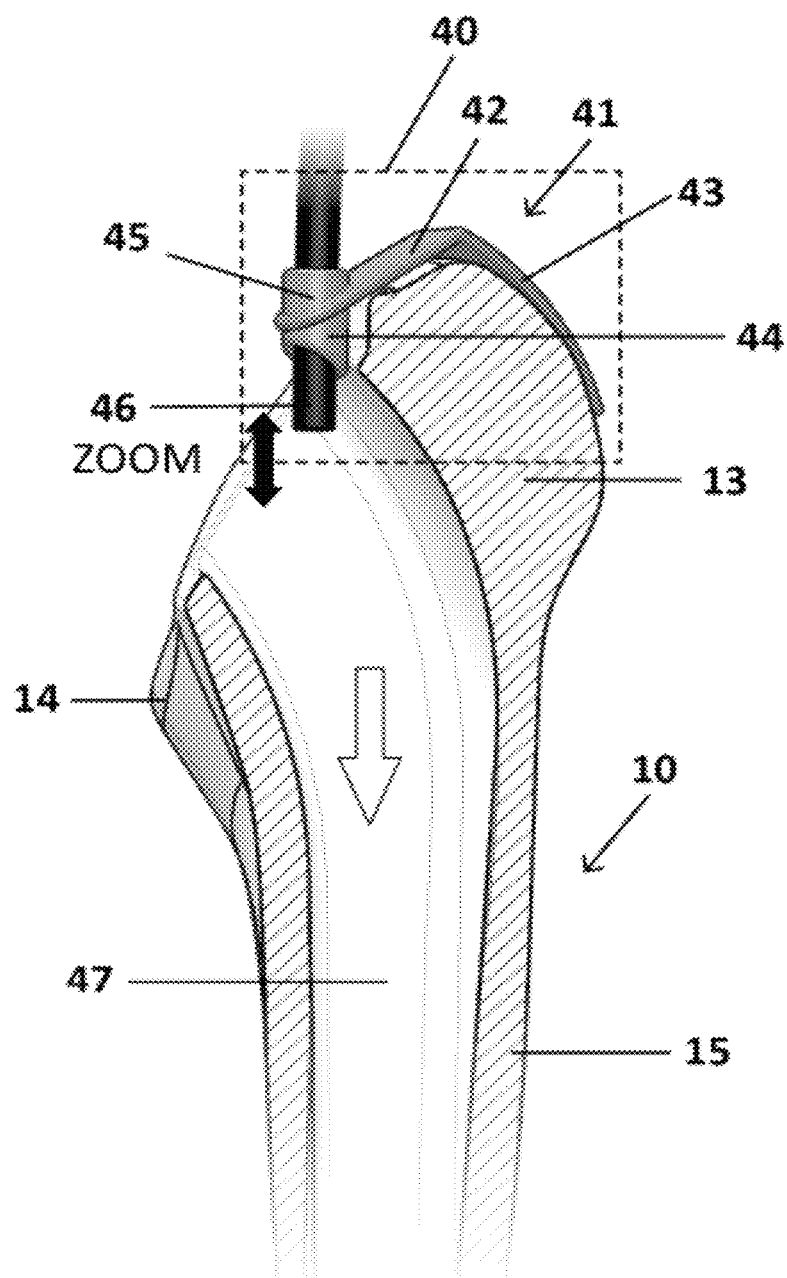
FIG. 19 illustrates a further embodiment of a mounting system according to the present invention, wherein a scope is arranged through an instrument holder.

In the embodiments illustrated in FIG. 4 and FIG. 19, the instrument holder 45 is a cylindrical tube adapted for receiving a scope. In alternative embodiments, not illustrated, the instrument holder may be of another type, such as for example a clipping device or a set of pincers. This allows to receive scopes, e.g. flexible scopes, from different origin, hence potentially having different diameters, while still being able to grasp them and keep them fixed in place.

Figure 16:
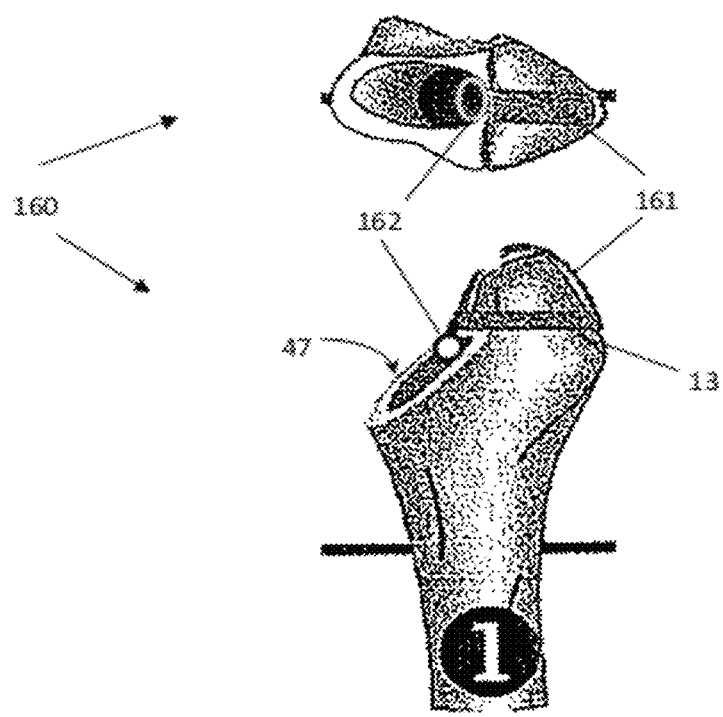
FIG. 16 to FIG. 18 illustrate further embodiments of a mounting system according to the present invention.

Another embodiment of a mounting system 160 according to the present invention is illustrated in FIG. 16, both in top view (top of FIG. 16) and in front view (bottom of FIG. 16). The mounting system 160 comprises a positioning system 161 adapted for being mechanically attached to a bone. In this particular embodiment, the positioning system 161 is a clamp adapted for being placed on, e.g. hung onto, the greater trochanter 13. The mounting system 160 furthermore comprises at least one instrument holder 162 attached to the positioning system 161, the instrument holder 162 being adapted for holding one or more instruments for being used during bone surgery in a medullary canal 47.

Figure 17:
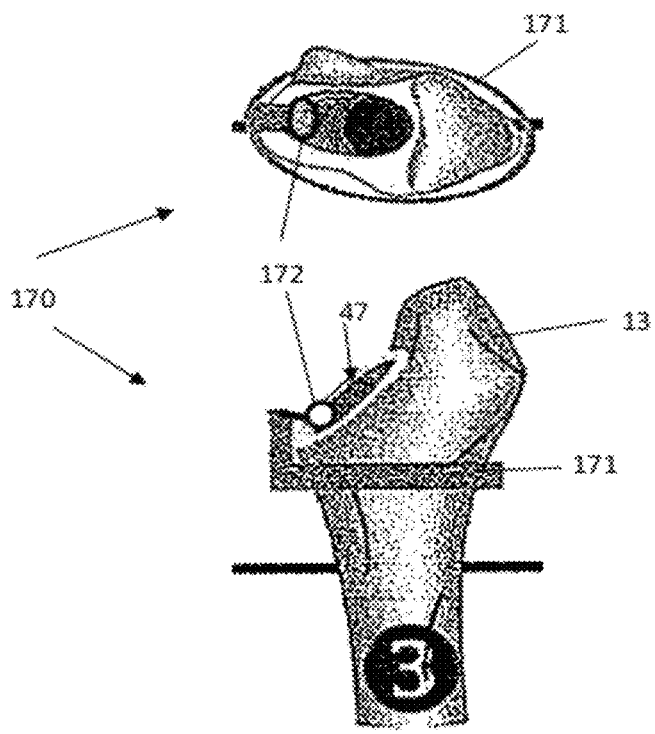

Yet another embodiment of a mounting system 170 according to the present invention is illustrated in FIG. 17, both in top view (top of FIG. 17) and in front view (bottom of FIG. 17). The mounting system 170 comprises a positioning system 171 adapted for being mechanically attached to a bone. In this particular embodiment, the positioning system 171 is a clamp or a clip adapted for being placed around the bone. The mounting system 170 furthermore comprises at least one instrument holder 172 attached to the positioning system 171, the instrument holder 172 being adapted for holding one or more instruments for being used during bone surgery in a medullary canal 47.

Figure 18:
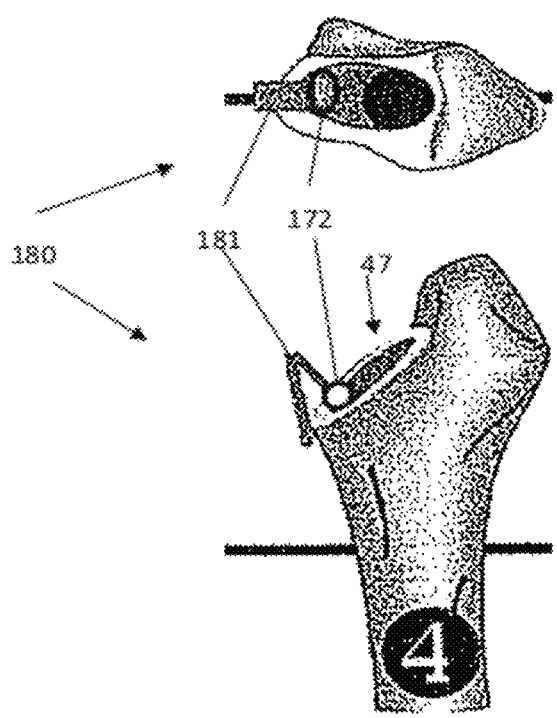

Still another embodiment of a mounting system 180 according to the present invention is illustrated in FIG. 18, both in top view (top of FIG. 18) and in front view (bottom of FIG. 18). The mounting system 180 comprises a positioning system 181 adapted for being mechanically attached to a bone. In this particular embodiment, the positioning system 181 is a clamp or a clip adapted for being clamped or clipped over a wall of the bone, more particularly over a sidewall of the medullary canal 47. The mounting system 180 furthermore comprises at least one instrument holder 182 attached to the positioning system 181, the instrument holder 182 being adapted for holding one or more instruments for being used during bone surgery in a medullary canal 47.

Figure 5:
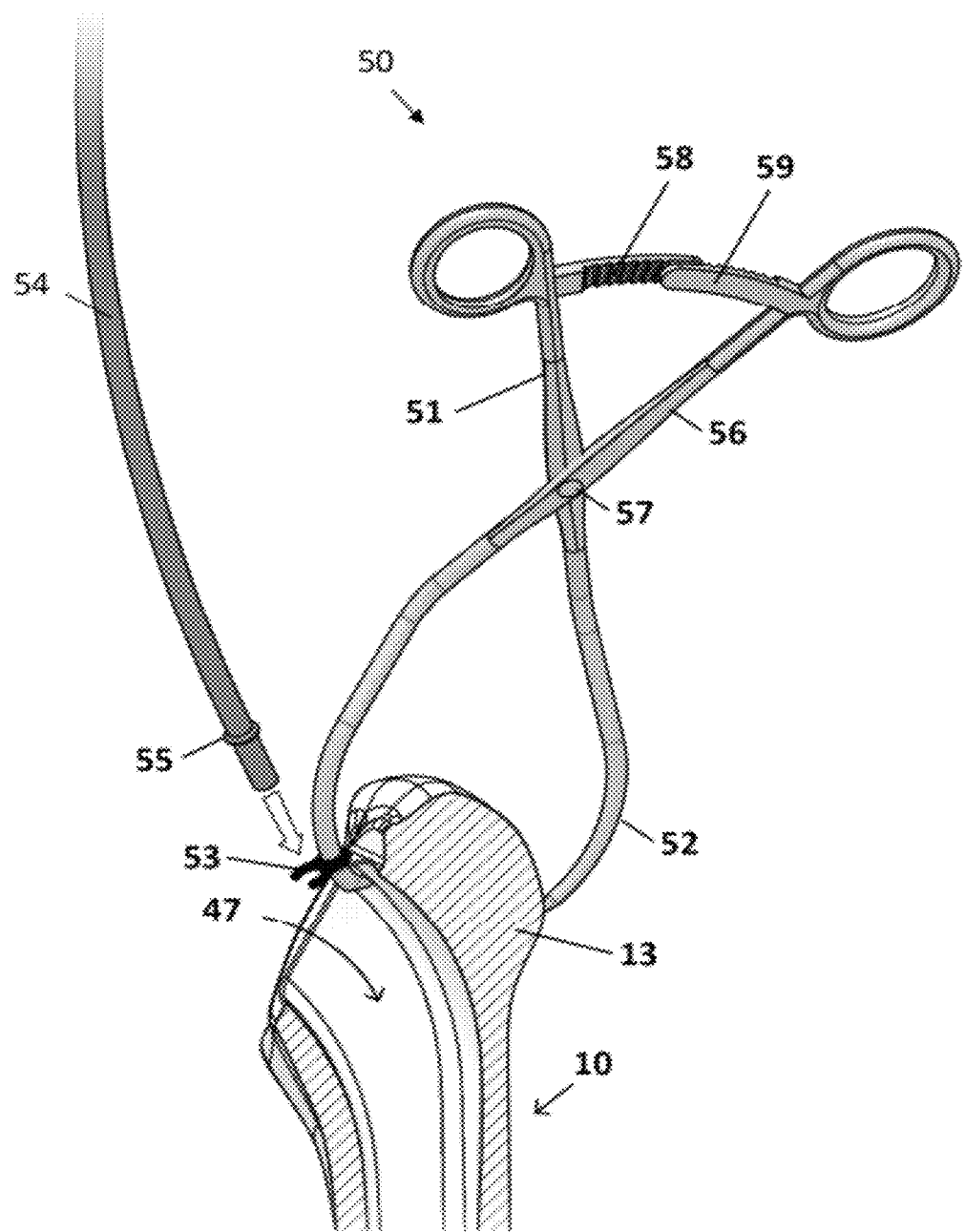
FIG. 5 illustrates a second embodiment of a mounting system according to the present invention.
Figure 6:
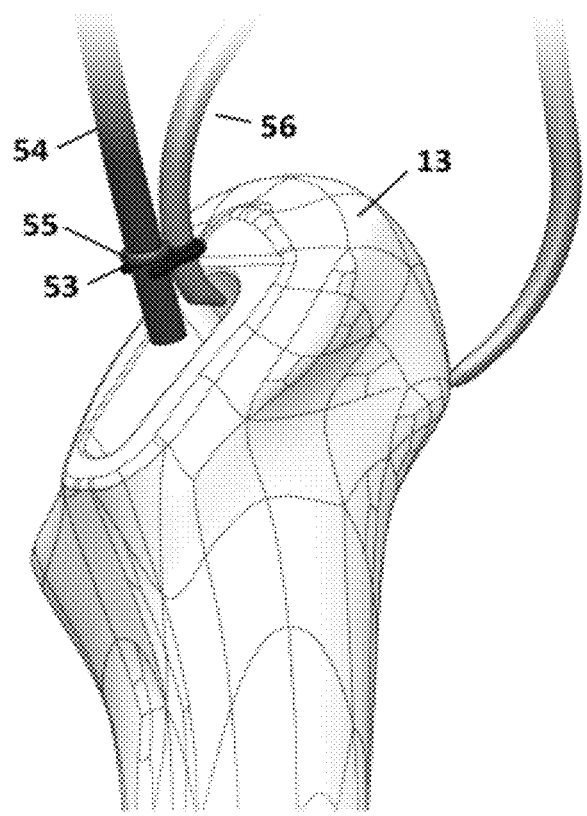
FIG. 6 is an enlarged 3D view of part of FIG. 5.

A further embodiment of a mounting system 50 according to embodiments of the present invention is illustrated in FIG. 5. This mounting system 50 comprises a positioning system 51 adapted for being mechanically attached to a bone, in the embodiment illustrated to the greater trochanter 13 of a femur 10. In the embodiment illustrated in FIG. 5, the positioning system 51 is provided with a nail or a nail-like extremity 52 for being mechanically attached, in casu nailed into the bone. In alternative embodiments, not illustrated, the positioning system 51 could comprise a screw threaded end for allowing the positioning system to be screwed into the bone 10. Furthermore, the mounting system comprises an instrument holder 53. In the embodiment illustrated in FIG. 5, the instrument holder 53 is a ring segment, adapted in shape and dimensions to allow an instrument, such as e.g. a scope 54, to pass through it at least partially. The scope 54 may be provided with a rib 55 adapted for being supported by the instrument holder 53, so that the instrument holder 53 is able to hold the instrument, e.g. scope 54, in place. This is illustrated in more detail in FIG. 6.

In the embodiment illustrated in FIG. 5, the instrument holder is mounted on an arm 56. The arm 56 of the instrument holder 53 and the positioning system 51 are mechanically connected to each other in a pivoting point 57. This means that the positioning system and the arm 56 of the instrument holder 53 can rotate with respect to each other around this pivoting point 57. In the embodiment illustrated, the arm 56 of the instrument holder 53 and the positioning system 51 form a scissorlike device. Two connector strap halves 58, 59 are provided between the positioning system 51 and the arm 56 of the instrument holder 53, a first connector strap halve 58 on the positioning system 51 and a second connector strap halve 59 on the arm 56 of the instrument holder 53. In the embodiment illustrated, the connector strap halves 58, 59 are each provided with a toothed surface. Both connector strap halves 58, 59 are mounted with their toothed surfaces oriented towards one another, so that a fixed position of the arm 56 of the instrument holder 53 with respect to the positioning system 51 can be obtained. These toothed strap halves 58, 59 allow to accurately position the instrument holder 53 with respect to the medullary canal 47, and hence allows to accurately position an instrument to be attached to the instrument holder 53 with respect to the medullary canal 47.

In alternative embodiments, not illustrated, rather than being implemented in a toothed version, a first one of the connector strap halves could be provided with a slit, while a second one could be provided with a screw and a nut, for example a wing nut, whereby the first and second connector straps are mounted such that the screw of the second connector strap is provided through the slit of the first connector strap. A fixed position of the instrument holder 53, via a fixed position of the arm 56 with respect to the positioning system 51 can be obtained by tightening the nut on the screw.

Figure 7:
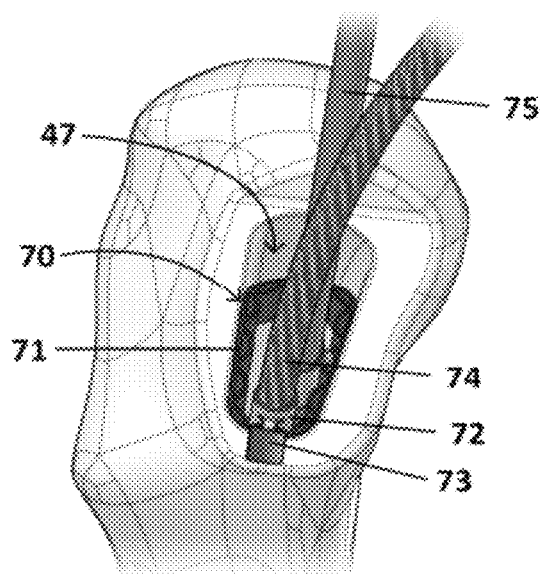
FIG. 7 illustrates a third embodiment of a mounting system according to the present invention.

A third embodiment of a mounting system 70 according to the present invention is illustrated in FIG. 7. The mounting system 70 comprises a positioning system 71, which in this embodiment is a spring, for example a metal spring, introduced into the medullary canal at the open top, and kept in place substantially at the top level by means of its resilience. Hence the spring is adapted for being fixed in the medullary canal. Optionally, in order for the spring 71 not to sink too deep into the canal, in particular when forces act on the spring because instruments are introduced into the medullary canal 47, a bridging piece 73 may be provided at a side of the spring 71, adapted for resting on the bone part forming the channel wall. Optionally, the bridging piece 73 may clip over the bone part forming the channel wall.

Figure 8:
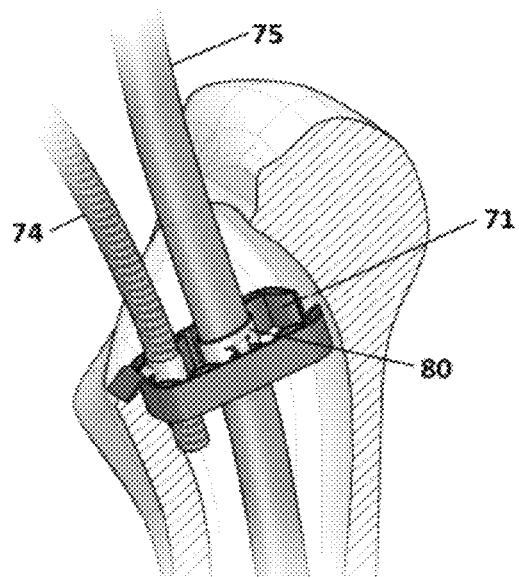
FIG. 8 shows a detail of an embodiment of an instrument holder which may be used in embodiments of the present invention.

On the spring 71, at least one instrument holder 72 is provided. In the embodiment illustrated in FIG. 7, the instrument holder 72 consists of a ring or ring segment into which one or more instruments, for example a scope 74 and/or a suction tube 75, can be held. In an alternative embodiment, the instrument holder 72 may comprise a plurality of rings, each attached to the positioning system 71, for each holding an instrument, for example for a scope 74 and a suction tube 75. Instead of one or more rings 72, one or more ring segments 80, for example as illustrated in the detail of FIG. 8, can also be used. Depending on the shape of the instrument to be used, the instrument holder may have a shape different from a ring or a ring segment. For example, the positioning system may be square, rectangular, polygonal, oval, or may have any other suitable shape. In particular embodiments, the positioning system may have any of the above shapes with an open side. In the embodiment illustrated in FIG. 8, the instrument holder is an attach clip 80 for holding a suction tube. In the embodiment of FIG. 8, the ring 72 for holding a scope 74 is not visible, although the scope 74 is.

Figure 9:
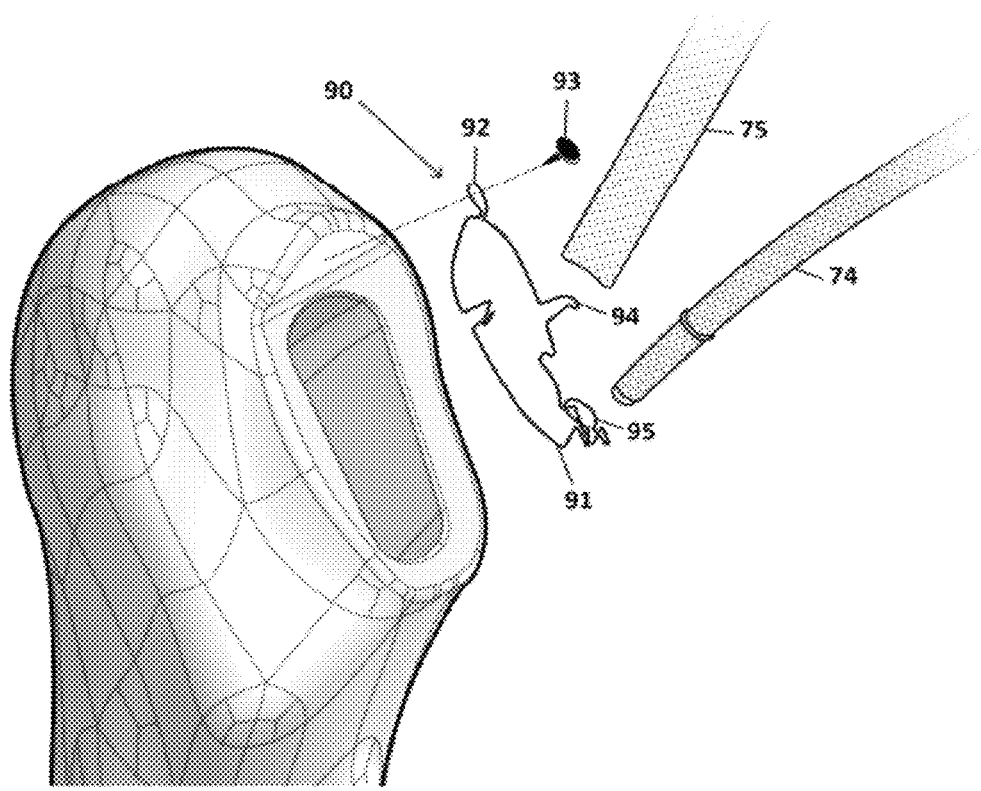
FIG. 9 and FIG. 10 illustrate a fourth embodiment of a mounting system according to the present invention, in non-operational and in operational position, respectively.
Figure 10:
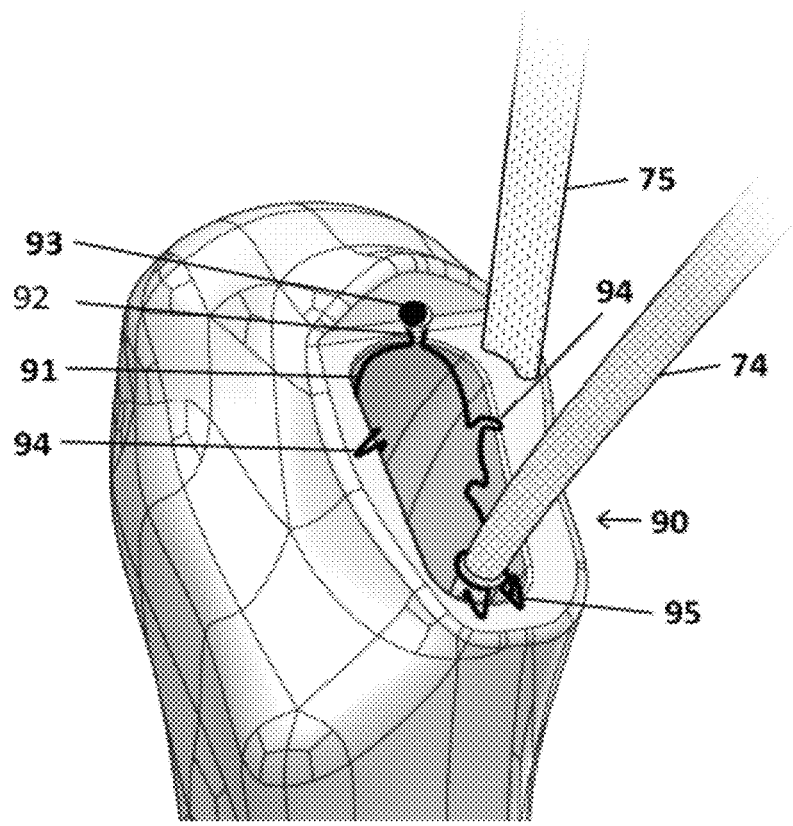

Yet another embodiment of a mounting system 90 according to the present invention is illustrated in FIG. 9 and FIG. 10.

The mounting system 90 comprises a positioning system 91 adapted for being mechanically attached to a bone. In the particular embodiment illustrated, the positioning system 91 is a bent wire, bent in a specific shape, for example a metal wire. The wire 91 is provided with a loop 92 so as to enable fixation thereof to the bone, for example by means of a pinning device such as a nail 93. The wire 91 may be bent so as to form arms 94 which are adapted to be supported by the canal wall, formed by the bone around the medullary canal 47 (not shown in FIG. 9 and FIG. 10). The wire 91 may furthermore be bent so as to form an instrument holder loop or hook 95 for holding one or more instruments. A plurality of instrument holder loops or hooks 95 may be provided on a single positioning system 91. The wire 91 may be such that it can be deformed by the surgeon when putting it in place, so as to fit it to the bone which is to be operated on.

Figure 11:
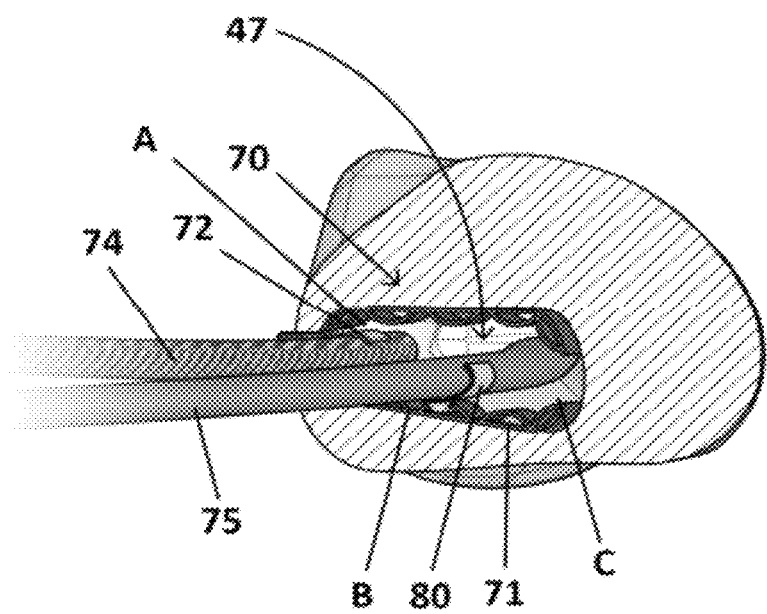
FIG. 11 is a top view of the third embodiment of a mounting system according to the present invention, placed into a medullary canal.

FIG. 11 shows a top view of a hollow bone onto which a mounting system 70 according to the third embodiment of the present invention is attached. This is by way of example only; the mounting system used could be any type of mounting system according to embodiments of the present invention. The mounting system 70 comprises a positioning system 71, in the embodiment illustrated a spring, mechanically attached to the bone by its resilience, a first instrument holder 72 for holding a scope 74 and a second instrument holder 80 for holding a suction device 75. It can be seen that, by using a mounting system 70 or any other mounting system according to embodiments of the present invention, instruments such as scope 74 and/or suction tube 75 are held in place by the mounting system 71 and allow the surgeon to operate on the bone without the need for holding these instruments by hand. Furthermore, the instruments are held fixed against the inner wall of the medullary canal 47, thus providing sufficient working space. The location A where the scope 74 is provided in the embodiment illustrated in FIG. 11 is the ideal scope zone, because it is out of the ideal working area, and it gives a good view into the medullary canal 47. The specific location is patient dependent. The ideal suction area A is at the side of the canal 47, because it is out of the ideal working area, and gravity causes blood collecting on the floor of the shaft. The location C is the ideal working area, because it is the best way substantially straight into the canal 47 with rigid instruments, and hence it allows the use of most existing tools. If the mounting system is to be attached to the femur by attachment means such as for example a nail, the greater trochanter is the best fixation place in view of its big voluminous bone.

It is an advantage of the embodiment illustrated in and/or described with respect to FIG. 11 that the scope is fixed so that the surgeon can work hands free. If the scope is positioned in its optimal position, it does not interfere with other instruments. The scope does not disturb the surgeon, neither does it disturb the assistants.

A mounting system according to embodiments of the present invention may be made from lightweight material, for example plastic. In particular embodiments, it may be made disposable, hence making it for example for single-time use.

Figure 12:
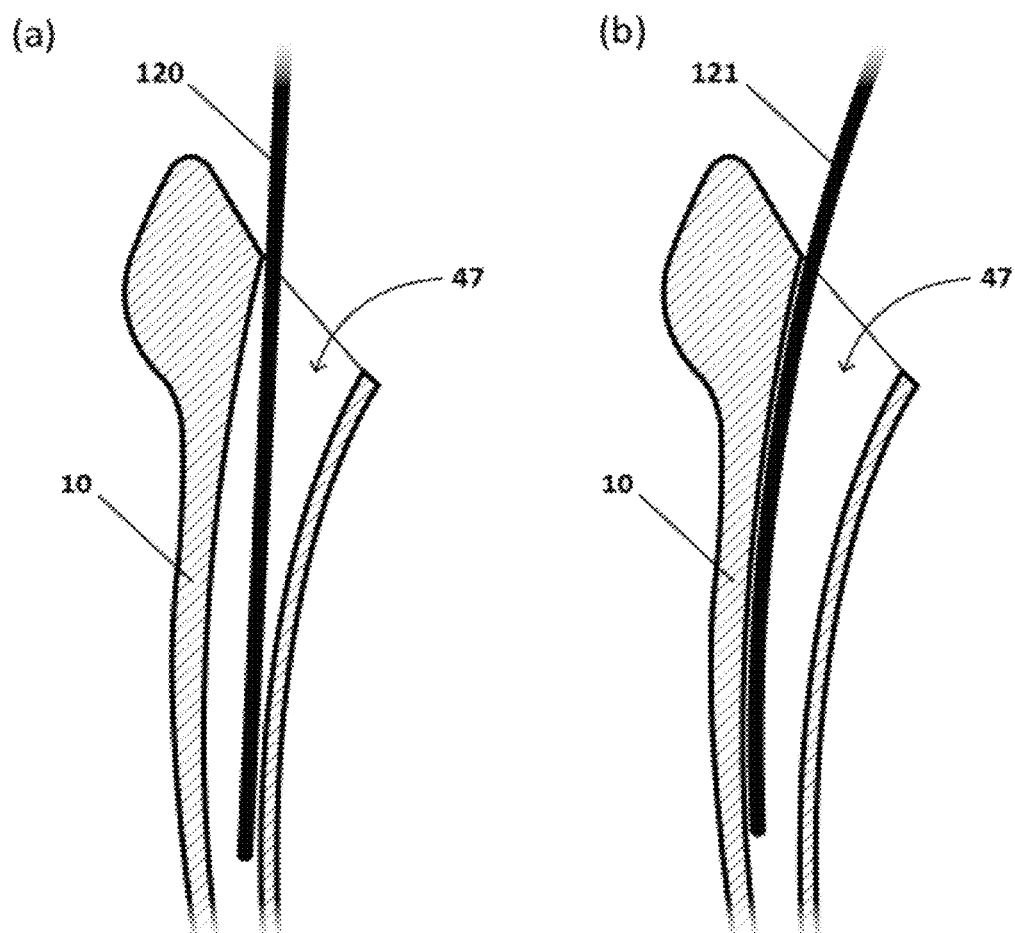
FIG. 12 illustrates the advantage of using a flexible scope (FIG. 12(b)) over using a stiff scope (FIG. 12(a)) in embodiments of the present invention.

In particular embodiments of the present invention, the scope which may be used is a flexible scope. The shape of the scope may be adapted to the anatomical canal of the bone. The advantage of using a flexible scope is illustrated in FIG. 12. FIG. 12(a) of this drawing illustrates a femoral bone 10 where a stiff scope 120 is introduced into the medullary canal 47, as known in the prior art. As can be seen, due to the bone 10 not being completely straight, the stiff scope 120 can only be introduced a limited depth into the medullary canal 47. Moreover, such stiff scope occupies a lot of space in the canal 47. When using a flexible scope 121, to the contrary, as illustrated in FIG. 12(b), the scope 121 can be shaped so as to reach the bottom of the canal 47, despite it being bowed. Moreover, the flexible scope 121 can be shaped so that it can be placed against an inner wall of the medullary canal 47, so that it occupies less space, thus leaving more free working space to the surgeon. As a flexible scope, fibre optics, for example with a length between 30 and 50 cm, or chip-on-tip laparoscopes may be used. These embodiments are advantageous as there is no need for the surgeon to hold and support a camera head.

Figure 13:
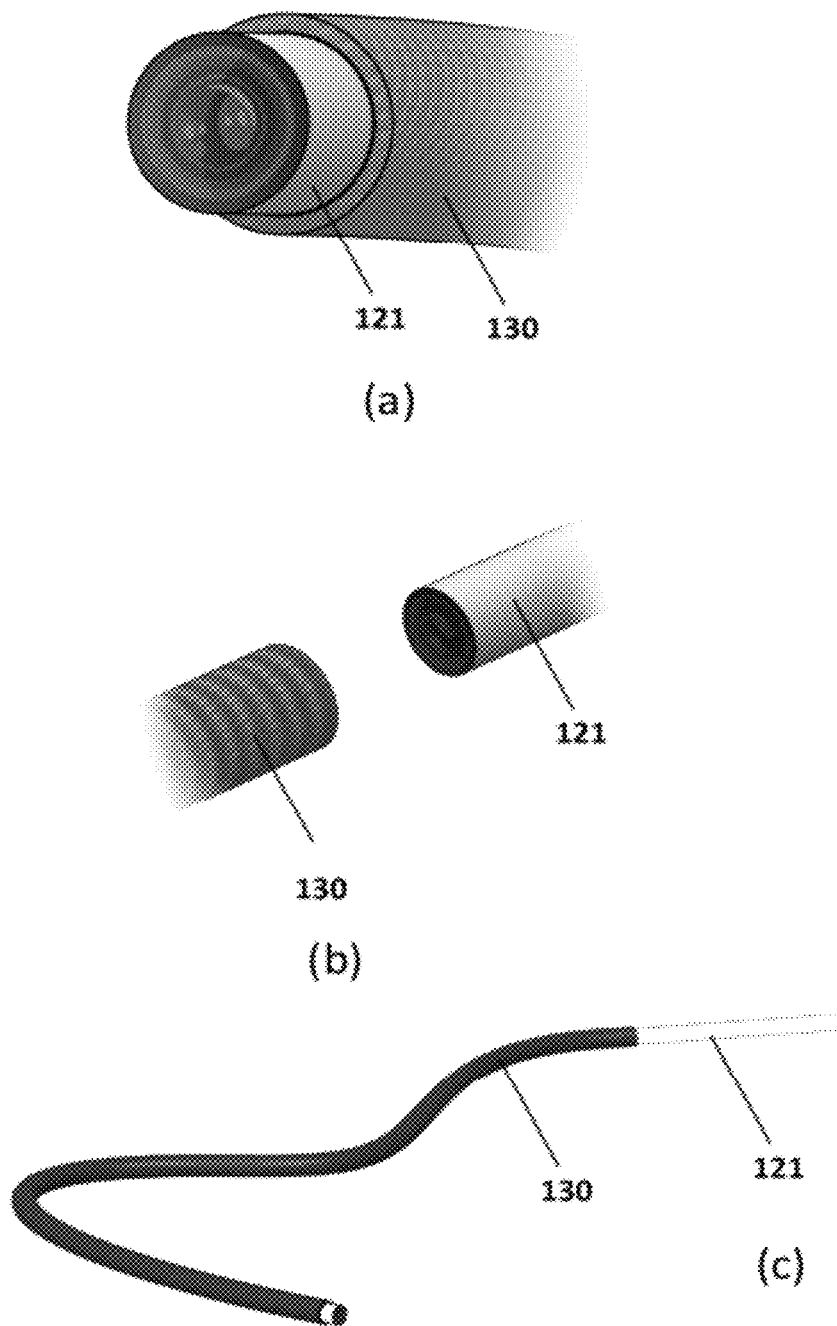
FIG. 13 illustrates a particular embodiment of a flexible scope mounted inside a protecting sleeve for use with a mounting system according to embodiments of the present invention.

In particular embodiments, as for example illustrated in FIG. 13, the flexible scope 121 may be protected against damage, such as for example scratching, e.g. by sharp and aggressive instruments such as chiseling instruments and high speed burrs used during surgical bone operation, or by rough handling. Such protection against damage can be provided by means of a protecting sleeve 130 around the flexible scope 121. The protecting sleeve 130 may furthermore be adapted for protecting against blood, water, and/or disinfectants. In particular embodiments, the protecting sleeve 130 may consist of wires, e.g. metal wires, around the flexible scope 121. If the wires have a memory function for flexure, the shape of the scope 121 may be adapted, for example by bending. This allows the placing against the inner wall of the canal 47 and the following of the canal 47 despite it being bowed, as indicated above. The protection of the flexible scope by means of a sleeve may be particularly useful in orthopedic use.

Figure 14:
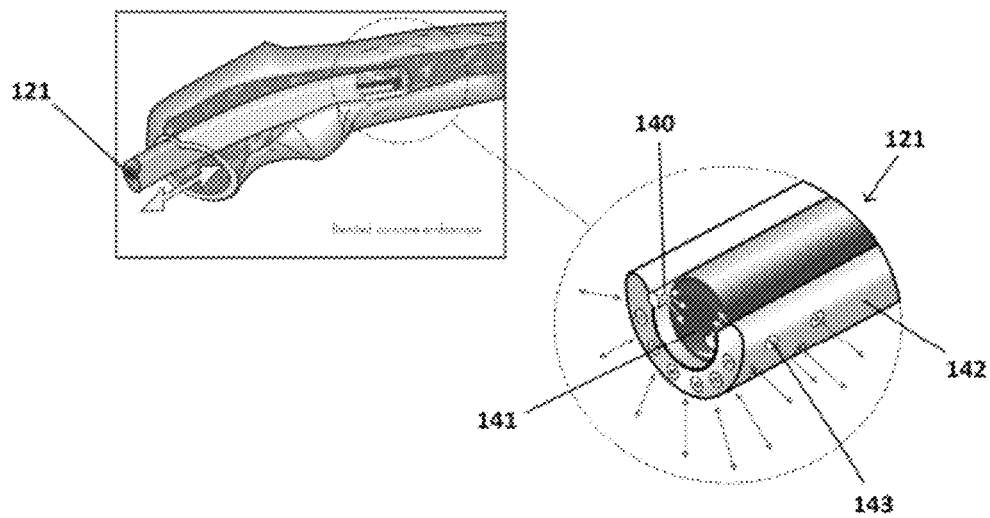
FIG. 14 illustrates an alternative embodiment of a flexible scope for use with a mounting system according to embodiments of the present invention.

In particular embodiments, as for example illustrated in FIG. 14, the scope 121 may be provided at its front side with a cleaning system 140 for cleaning the lens 141. One embodiment is a flushing system, comprising means for flushing and suction and drying. In particular embodiments, flushing is permitted only intermittently. In an alternative embodiment, such cleaning system may comprise a gas blowing system, e.g. blowing air or $CO_2$, optionally provided in a protective sleeve 142 around the flexible scope 121.

In particular embodiments of the present invention, not illustrated in the drawings, at the tip of the scope a cleaning system, for example a suction system, could be provided for cleaning the canal, e.g. by removing fluid such as blood. Nevertheless, it is advantageous to provide a cleaning system for cleaning of the lens 141 of the scope (e.g. an air blowing system as explained with respect to FIG. 14) separate from a cleaning system for canal cleaning (e.g. a separate suction tube as for example in FIG. 11), rather than performing canal cleaning with the cleaning system provided at the tip of the scope (a suction system), because in the latter case the scope needs to be dipped in the fluid to be removed, leading to reduced visibility of the inside of the canal 47.

In particular embodiments, also illustrated in FIG. 14, light sources 143 may be provided in the protective sleeve 142, to direct light towards a scene to be recorded and/or to direct light in front of the lens 141 of the scope 121.

Figure 15:
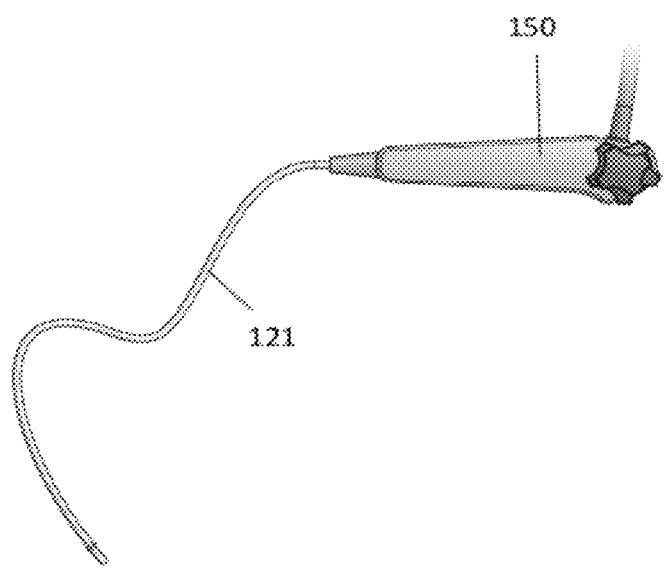
FIG. 15 illustrates a camera system attached to a scope according to embodiments of the present invention.

A camera 150 may be provided at one extremity of the flexible scope 121, as illustrated in FIG. 15. Optical cables may be provided between the front extremity of the scope 121 and the camera 150.

According to one aspect, the present invention provides an endoscopic resection system, as for example illustrated in FIG. 11, comprising a mounting system according to any of the mounting system embodiments of the present invention, in the case illustrated a mounting system 70 according to the third embodiment, and an endoscope 74 for visualizing the medullary canal 47. The endoscope 74 may be a flexible scope, for example a flexible scope as illustrated in FIG. 13, FIG. 14 or FIG. 15. Such endoscopic resection system allows minimally invasive medical procedures, in particular in case of endoscopically assisted bone surgery, for example hip arthroplasty surgery.

An ideal scope for use with a resection system according to embodiments of the present invention has one or more of the following features: a small diameter so as to allow maximum working space, provides high image quality, is flexible, is light weight, ergonomic, can be used hands free so that the surgeon can use both hands for operating, is autoclavable, is orthopedic proof, hence scratch resistant, looks in a forward direction (0° lens) so as to not lose orientation, and/or is not too expensive.

The endoscopic resection system may furthermore comprise a suction tube 75 (see e.g. FIG. 7) for removal of fluids like for instance blood.

In embodiments of the present invention, the endoscopic resection system may furthermore comprise a powered device, such as for example but not limited thereto a chiseling instrument, a drill.

Endoscopic resection systems according to embodiments of the present invention may be used during bone surgery, for example but not limited thereto during surgery on medullary bones, e.g. hip surgery.

During experimental surgical operations, patients were positioned in lateral decubitus. Femoral sizing and offset was planned on the preoperative radiographs using acetate templates both in the anteroposterior and lateral view. A minimal invasive anterolateral exposure was used in all patients.

After femoral neck resection, the medullary canal was opened using a Charnley awl with a blunt tip. Standard available femoral broaches (Spectron, Smith & Nephew—Memphis) were used to gradually widen the femoral canal until sufficient rotational stability of the broach was obtained. Suction of the femoral canal was performed after insertion of the awl and after insertion of every broach to remove blood and marrow from the femoral canal and improve the medulloscopy. After trial reduction the broach was removed and a universal cement restrictor (Prep-IM kit, Smith & Nephew—Memphis) was inserted. The classic steps of third generation cement technique were used in all patients. Bone bed preparation consisted of brushing, pulsed lavage with saline and insertion of a canal filling tampon with suction (Prep-IM kit, Smith & Nephew—Memphis) 20 to 60 seconds before femoral cement insertion.

Gentamycine loaded Palacos (Heraeus Medical, Germany) was used in all cases using a cement gun for retrograde filling of the canal. A 10 mm diameter, 0° forward looking laparoscope (Strotz, Germany) was selected to perform the medulloscopy. The laparoscope was held at the inner side of the greater trochanter allowing visual inspection of the medullary canal while working inside the canal at the same time. The used endoscopic equipment consisted of a Trinitron monitor (model PVM20M2MDE, SONY), a Storz camera (TELECAM 20212030, Karl STORZ) and control unit (TELECAM SL Pal 20212020, Karl STORZ), a cold light fountain (XENON NOVA 20131520, Karl STORZ), a fibre glass light conducting cable (495NCS, Karl STORZ) and several Hopkins lenses. The following Karl STORZ lenses were used: two 0° forward view 5 and 10 mm in diameter (Models 26006AA and 26003AA res.) and one 30° forward oblique view 5 mm in diameter (Model 28031BA).

Endoscopic findings were recorded on videotape and video print. The femoral canal was divided in four zones consisting of the roof between the 10 and 2 o'clock position, two side walls between 2 and 4 and 8 and 10 o'clock position and the floor between the 4 and 8 o'clock position.

Medulloscopy of the femoral canal was performed in 6 different stages of the canal preparation: after insertion of Charnley awl, after insertion of the last broach, after brushing, after pulsed lavage, after insertion of the canal filling tampon with suction and finally just before the insertion of the cement.

The cleanliness of the canal and the rate of intramedullary bleeding were standardised on a 4 point scale (table 1) going from a grade 0 canal with perfectly dry cancellous bone to a grade Ill canal with arterial intramedullary bleeding.

TABLE I

| Grade | Bleeding type |
| --- | --- |
| Grade 0 | No bleeding, cancellous bed of the shaft completely dry, trabecular lacunae are empty in zone 1, 2 and 3, no pooling of blood in the gutter or distally at the cement restrictor. Excellent visualization of the whole femoral canal, appearance of a dried 'cadaver femur'. |
| Grade I | Oozing from the cancellous bone in zone 1 and 2, slow filling of the floor between the 5 and 7 o'clock position, regular suction necessary, good visualization of the shaft is possible, small pooling of blood and fat at the distal restrictor. |
| Grade II | Moderate bleeding in zone 1 and 2, rapid filling of the floor between the 4 and 8 o'clock position, very frequent suction necessary to maintain visualization of the shaft, quick pooling of blood obstructing visualization of the cement restrictor. |
| Grade III | Rapid and complete filling of the canal, same as grade II but also pulsating arterial bleeding. |

When intramedullary arterial bleeding occurred, this was controlled using a long tip standard diathermy tip.

Orthowave™ software was used for clinical data collection.

A non-parametric repeated measures ANOVA was used for statistical analysis. repeated measures with posthoc Dunn's test to correct for multiple comparison The patient population consisted of 178 (68% female and 32% male) patients available for follow-up. 92 patients (51%) were operated on the right side and 86 (49%) on the left side.

The indication for total hip arthroplasty was osteoarthritis of the hip (102 cases, 57.3%), subcapital fracture of the hip (60 cases, 33.7%), osteonecrosis of the femoral head (9 cases, 5.1%), rheumatoid arthritis of the hip (4 cases, 2.2%) and not specified in the above (3 cases, 1.7%).

A surgical technique was performed, which comprised the following steps. Patients were placed in the lateral decubitus position. An anterolateral, transgluteal (Hardinge) approach was used. Multiple cultures were taken after the incision of the fascia and arthrotomy of the hip and cultures were also obtained from the excised membrane and the medullary canal. The following sequential operative steps were used for implant and cement removal:

1. Removal of cement from between the greater trochanter and the shoulder of the prosthesis to allow for stem extraction.
2. Extraction of the implant stem using extraction instruments.
3. Endoscopic evaluation of the existing cement mantle.
4. Removal of all accessible proximal cement using narrow osteotomes and chisels of various sizes and thicknesses.
5. Radial and longitudinal splitting of the metaphyseal cement and removal thereof using a variety of grasping instruments. At this stage a 10 mm laparoscope was used as an additional light source.
6. Positioning of a helix ultrasound tool under endoscopic control.
7. Perforation of the distal cement plug using ultrasound.
8. Inspection of plug perforation with a 5 mm laparoscope after cleaning and washing out the canal using pulsed lavage.
9. Advancement of a ball-tipped guide wire into the distal part of the femur.
10. Positioning of a guide wire using the image intensifier.
11. Reaming of the well-fixed cement mantle in 0.5 mm increments using a standard flexible cannulated low pressure intramedullary reamer. The canal was washed out after every reamer passage and the canal was inspected using the 5 mm laparoscope.
12. Ultrasonic driven curettes were used to remove remaining cement from side-walls.
13. After the cement had been completely removed, the membrane lining the medullary canal was meticulously curetted out under endoscopic control.
14. Before placement of cementless revision stems with distal fixation, reaming and sizing of the distal femur were performed under endoscopic control.

When using the laparoscope, a mounting system according to embodiments of the present invention was used in order to fix the scope so that it can be used hands free, so that the surgeon can use both hands for operating.

It has been noted that 5 mm and 10 mm laparoscopes with a 0° lens angle are the best choice when standard equipment is used for medulloscopy. Endoscopes with angled lenses can cause incorrect orientation of instruments inside the canal and increase the risk for perforation.

The mounting system according to embodiments of the present invention, as well as the endoscopic resection system according to embodiments of the present invention may be used in all applications where bone endoscopy is performed. As described above, a method and device according to embodiments of the present invention may be used in hip arthroplasty. Alternatively, they may be used for dynamic hip screw replacement, for retrieval of broken instruments and/or nails from the bone canal, for fracture repositioning. It is advantageous that these operations can be performed in a minimally invasive manner.

While the invention has been illustrated and described in detail in the drawings and foregoing description, such illustration and description are to be considered illustrative or exemplary and not restrictive. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to include any specific characteristics of the features or aspects of the invention with which that terminology is associated.

The invention claimed is:

1. A mounting system for holding one or more instruments for use in medulloscopy in a medullary canal, the mounting system comprising:
    a positioning system configured to be mechanically attached to a bone with a removed head having an open medullary canal in the bone, and at least one open instrument holder attached to the positioning system, the instrument holder being configured to hold at least one instrument used during bone surgery fixed against an inner wall of the medullary canal,
    wherein the positioning system has a shape adapted for being supported by an upper part of the bone with the removed head or an upper surface of the open medullary canal, and
    wherein the mounting system comprises a completely open working space for a user between the inner wall and the at least one instrument being on an opposite side of the inner wall of the open medullary canal in the bone, when the instrument holder is used during bone surgery and at least one instrument is held by the instrument holder.

2. An endoscopic resection system comprising:
    the mounting system recited in claim 1, and an endoscope enabling visualization of a medullary canal.

3. The endoscopic resection system according to claim 2, wherein the endoscope is a flexible scope.

4. The endoscopic resection system according to claim 3, wherein the flexible endoscope includes a sleeve that protects the scope during surgical use.

5. The endoscopic resection system according to claim 4, wherein the sleeve has a memory function for flexure.

6. The endoscopic resection system according to claim 2, comprising a suction tube.

7. The endoscopic resection system according to claim 2, comprising a powered device.

8. The endoscopic resection system according to claim 7, wherein the powered device is a drill.

9. A method of using a mounting system according to claim 1 or of an endoscopic resection system according to claim 2 in orthopedic surgery, hip surgery, hip arthroplasty, or pelvic surgery, comprising:
    providing the mounting system which comprises a positioning system and at least one instrument holder,
    mechanically attaching the positioning system to the upper part of the bone with the removed head or the upper surface of the open medullary canal in the bone, at least one instrument holder being attached to the positioning system, and
    attaching one or more instruments to the at least one instrument holder, so as to hold the one or more instruments used during bone surgery fixed against an inner wall of a medullary canal forming the completely open working space for a user between an opposite side of the inner wall and the one or more instruments fixed against the inner wall of the open medullary canal in the bone for introducing instruments in the medullary canal.

10. The mounting system according to claim 1, wherein the positioning system is a bent wire arranged to be attached onto the bone.

11. The mounting system according to claim 10, wherein the bent wire is a loop formed in a way such that the bent wire has at least one arm configured to be supported by a canal wall of the open medullary canal, at least one loop or hook forming the instrument holder, and at least one loop configured to enable fixation to the bone.

12. A mounting system for holding one or more instruments for use in medulloscopy in a medullary canal, the mounting system comprising:
    a positioning system configured to be mechanically attached to a bone, and at least one instrument holder attached to the positioning system, the instrument holder being configured to hold one or more instruments used during bone surgery fixed against an inner wall of the medullary canal,
    wherein the positioning system comprises a spring system fixable in the medullary canal.

13. A method for preparing a minimally invasive method for performing bone surgery, the preparation method comprising:
    mechanically attaching a positioning system to an upper part of a bone with a removed head or an upper surface of an open medullary canal in the bone, with an instrument holder being attached to the positioning system,
    attaching one or more instruments to be used during bone surgery to the instrument holder in the medullary canal such that the one or more instruments are held fixed against an inner wall of the medullary canal to form a completely open working space for a user between an opposite side of the inner wall and the one or more instruments fixed against the inner wall of the open medullary canal in the bone.

* * * * *